(12) United States Patent
Montcuquet

(10) Patent No.: US 9,301,686 B2
(45) Date of Patent: Apr. 5, 2016

(54) AUTOFLUORESCENT ORGAN PHANTOM AND ASSOCIATED METHOD OF PRODUCTION

(75) Inventor: Anne-Sophie Montcuquet, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 830 days.

(21) Appl. No.: 13/518,383

(22) PCT Filed: Dec. 22, 2010

(86) PCT No.: PCT/EP2010/070460
§ 371 (c)(1),
(2), (4) Date: Jun. 21, 2012

(87) PCT Pub. No.: WO2011/076829
PCT Pub. Date: Jun. 30, 2011

(65) Prior Publication Data
US 2012/0256127 A1 Oct. 11, 2012

(30) Foreign Application Priority Data
Dec. 24, 2009 (FR) ...................................... 09 59560

(51) Int. Cl.
*A61B 5/00* (2006.01)
(52) U.S. Cl.
CPC ............ *A61B 5/0059* (2013.01); *A61B 2503/40* (2013.01); *A61B 2560/0233* (2013.01)

(58) Field of Classification Search
CPC ...... A61B 8/587; A61B 8/08; A61B 2503/40; A61B 2560/0233; A61B 5/0059
USPC .......................................... 250/252.1, 301.16
See application file for complete search history.

(56) References Cited

U.S. PATENT DOCUMENTS

2003/0092986 A1* 5/2003 Sjoblom ........................ 600/437
2004/0067591 A1* 4/2004 Madsen et al. .................... 436/8

FOREIGN PATENT DOCUMENTS

DE 19855853 A1 6/2000
WO 2008/028298 A1 3/2008

OTHER PUBLICATIONS

Alec M. De Grand et al.: "Tissue-like phantoms for near-infrared fluorescence imaging system assessment and the training of surgeons," Journal of Biomedical Optics, vol. 11, No. 1, Jan. 2003.
Laure S. Fournier et al.: "In-vivo NIR autofluorescence imaging of rat mammary tumors," Optics Express, vol. 14, No. 15, Jul. 24, 2006, pp. 6713-6723.

(Continued)

*Primary Examiner* — Mark R Gaworecki
(74) *Attorney, Agent, or Firm* — Baker Hostetler LLP

(57) ABSTRACT

A calibration device for instrumentation for medical imaging, also called a "phantom," including a matrix. The calibration device includes at least one additive for simulating the autofluorescence properties of an organ or of a living tissue in the spectral band covering the red and near infrared, said additive belonging to the porphyrin class, such as protoporphyrin IX.

13 Claims, 4 Drawing Sheets

(56) References Cited

OTHER PUBLICATIONS

Petras Juzenas et al.: "Fluorescence spectroscopy of normal mouse skin exposed to 5-aminolaevulinic acid and red light," Journal of Phtotochemistry and Photobiology B: Biology, vol. 61, No. 1-2, Aug. 15, 2001, pp. 78-86.

Karsten Konig et al.: "In-vivo fluorescence detection and imaging of porphyrin-producing bacteria in the human skin and in the oral cavity for diagnosis of acne vulgaris, caried, and squamous cell carcinoma," Advances in Laser and Light Spectroscopy to Diagnose Cancer and Other Diseases, vol. 2135, No. 1, Jan. 1, 1994, pp. 129-138.

* cited by examiner

AUTOFLUORESCENT ORGAN PHANTOM AND ASSOCIATED METHOD OF PRODUCTION

CROSS-REFERENCE TO RELATED APPLICATIONS

This application is a National Stage of International patent application PCT/EP2010/070460, filed on Dec. 22, 2010, which claims priority to foreign French patent application No. FR 0959560, filed on Dec. 24, 2009, the disclosures of each of which are incorporated by reference in their entireties.

FIELD OF THE DISCLOSED SUBJECT MATTER

The field of the invention is that of calibration devices also called "phantoms" for reproducing certain characteristics of a biological tissue and in particular its optical properties. They are used, for example, for calibrating and evaluating the performance of instruments for medical imaging and algorithms for processing the images produced by these instruments. The phantom is a volume which can be liquid or solid or semi-solid or gelatinous. It is composed of various ingredients.

BACKGROUND

The use of optical phantoms has the advantage that it avoids many manipulations on laboratory animals such as mice or rats. Thus, the animals themselves are spared. There is also the saving of the time spent preparing for manipulations of this kind, which require considerable administration, permissions for obtaining and using systems appropriate to the animals for anaesthetizing them and keeping them unconscious during the operations.

These phantoms are used, in particular, for simulating the optical properties of tissues in ranges of wavelengths in the red and near infrared. In medical imaging, this wavelength range is interesting since the absorption of living tissues is less in this band of the spectrum. More precisely, a spectral window of interest is defined, located between the wavelengths of 600 nanometres and 900 nanometres.

Conventionally, the procedure for working in this band of the spectrum, as illustrated in FIGS. 1 and 2, is as follows. A specific marker M is injected in a patient or an animal S in the case of experiments (a mouse in FIG. 1). This marker M attaches specifically to the cancerous tumour T. The zone of interest is illuminated with a laser having an excitation wavelength in the red and a fluorescence signal is recovered. The laser excitation signal L is represented by a descending arrow in FIG. 1 and the fluorescence signal is represented by ascending arrows. This signal is a mixture of specific fluorescence $F_S$ (grey ascending arrows in FIG. 1) derived from the injected markers but also from autofluorescence $F_A$ (white ascending arrows in FIG. 1), i.e. natural fluorescence from biological tissues. In this wavelength range, the autofluorescence from tissues, per unit volume, is relatively slight, but it is sufficiently troublesome to drown the fluorescence signal, notably when the latter is weak. This is notably the case when a fluorophore is located deep inside a tissue.

FIGS. 2A, 2B and 2C show, as a function of the wavelength, the intensity I of the signal from specific fluorescence $F_S$, the signal from autofluorescence $F_A$ and the measured fluorescence signal $F_T$, which is composed of the two preceding signals. As can be seen in FIG. 2C, the measured fluorescence signal $F_T$ can be seriously disturbed by the signal from autofluorescence $F_A$.

It is therefore useful, if a "phantom" is required to be representative of a biological tissue in a range of wavelengths, and notably in the window of interest defined above, if it also possesses fluorescence characteristics representative of the autofluorescence of the tissue. Now, the origin of the autofluorescence from tissues is not yet known completely and quite particularly in this range of red or infrared wavelengths.

The biological tissues have a complex structure and comprise numerous components. We may mention, among others, collagen and elastin proteins, various amino acids such as tryptophan, agents such as NADH (nicotinamide adenine dinucleotide), lipo-pigments, components such as pyridoxine, enzymes such as flavine and other components such as the porphyrins. All these components, whose molecular structure can be very complex, may fluoresce in the visible spectrum.

Moreover, spectral differences may be observed in one and the same living being. In fact, there are structural differences between the anatomic localizations which may be reflected in variations of the form and intensity of the autofluorescence spectra. These differences vary from one individual to another.

Consequently, it is not a simple matter to produce a "phantom" that is representative of an organ or of biological tissues possessing characteristics of autofluorescence identical or similar to those of organic tissues.

SUMMARY

Experimental studies conducted by the applicant showed on the one hand that the fluorescence properties of compounds belonging to the porphyrin class are very close to the autofluorescence of biological tissues observed in the spectral window of interest and that, on the other hand, calibration devices or "phantoms" incorporating porphyrin also have fluorescence properties very similar to those of the autofluorescence of biological tissues.

Here, the term "properties" means the wavelength spectrum of the fluorescence emitted following excitation of a red wavelength, such a wavelength typically being between 620 and 800 nm.

More precisely, the invention relates to a calibration device for instrumentation for medical imaging also called a "phantom" comprising a matrix, characterized in that said matrix comprises at least one additive for simulating the autofluorescence properties of a living tissue in the spectral band covering the red and near infrared, said additive belonging to the porphyrin class.

Advantageously, the additive is protoporphyrin IX and the proportion of additive in the matrix is between 1 and 1000 millionths, preferably between 1 and 100, and more preferably between 30 and 60 millionths.

Advantageously, the matrix comprises a second additive, called an absorber, for simulating the optical absorption, and said second additive can be Indian ink or haemoglobin.

Advantageously, the matrix comprises a third additive, called a diffuser, for simulating optical diffusion, such as Intralipid or white paint or particles of oxide, such as $SiO_2$.

Advantageously, the matrix comprises a fourth additive, for increasing the viscosity, called a viscosity additive, such as a hydrogel, agarose gel, PVA (polyvinyl alcohol) or gelatin, for example food-grade gelatin.

According to one embodiment, the calibration device contains a tumour simulator.

According to a preferred embodiment, the matrix comprises a liquid, such as water, to which the aforementioned additives can be added. However, other aqueous solutions, for example saline buffers, can be contained in the matrix.

The invention also relates to a method of production of a calibration device or "phantom" for instrumentation for medical imaging, said calibration device comprising at least one matrix made according to at least the following stages:

- heating of a volume of liquid, for example water or saline buffer, to a temperature between 30 and 40 degrees;
- addition of a viscosity additive, such as sheets of gelatin softened in said volume of water and mixing until the sheets have melted completely, the amount of gelatin being between 4 to 8% of the volume of water;
- cooling the mixture of water and viscosity additive to room temperature;
- addition of an amount of a diffuser, for example Intralipid, white paint or a solution containing oxide beads, between 4 to 8%, preferably 5 to 6% of the volume of water when it is Intralipid 20%;
- addition of an amount of an absorber, for example Indian ink or haemoglobin, between 4 to 8% of the volume of water when it is Indian ink;
- addition of a fluorescent additive belonging to the porphyrin class in a proportion between 1 to 1000 millionths of the volume of water and preferably 30 to 60 millionths;
- cooling the liquid-viscosity additive-diffuser-absorber-additive mixture to a temperature of about 4° C. until the mixture hardens;
- removal of the mixture from the mould.

Preferably, the fluorescent additive used is protoporphyrin IX.

BRIEF DESCRIPTION OF THE DRAWINGS

The invention will be better understood and other advantages will become apparent on reading the following description, which is non-limiting, and the appended drawings, where:

FIGS. 2A, 2B and 2C show respectively the spectra of specific fluorescence, of autofluorescence and the measured spectrum, in which the spectra of autofluorescence and of specific fluorescence are combined.

DETAILED DESCRIPTION

The applicant hypothesized that the autofluorescence of healthy tissues could be simulated using a phantom comprising protoporphyrins. The applicant also showed that a particular type of porphyrins, which is present notably in the composition of haemoglobin, is particularly promising for simulating the phenomena of autofluorescence, namely protoporphyrin IX. Finally, the applicant demonstrated experimentally that the production of phantoms comprising porphyrins and notably protoporphyrin IX, designated Pp IX, did indeed have, under red illumination, a spectrum of fluorescence radiation comparable to the spectrum of autofluorescence of living tissues, in this instance those of laboratory mice.

This research was not obvious. In fact, certain authors consider that the concentration of porphyrin in animal tissues is too low to explain autofluorescence. Some others consider that other explanations are possible for explaining fluorescence. We may mention, in particular, necroses or bacterial infections, which may comprise components possessing properties of autofluorescence.

Reference may be made to the articles of Juzenas, of König and of Fournier for any additional information on these various points. The references of these articles are:

Petras Juzenas, Vladimir Iani, Saulius Bagdonas, Ricardas Rodomskis & Johan Moan "Fluorescence spectroscopy of normal mouse skin exposed to 5-aminolaevulinic acid and red light", Journal of Photochemistry and Photobiology B: Biology, Vol. 61, No. 1-2, pages 78-86, 2001;

Karsten König, Herbert Schneckenburger, Joerg Hemmer, Bruce J. Tromberg & Rudolf W. Steiner "In-vivo fluorescence detection and imaging of porphyrin-producing bacteria in the human skin and in the oral cavity for diagnosis of acne vulgaris, caries, and squamous cell carcinoma" Advances in Laser and Light Spectroscopy to diagnose Cancer and Other Diseases, Vol. 2135, No. 1, pages 129-138, 1994

Laure S. Fournier, Vincenzo Lucidi, Kirill Berejnoi, Theodore Miller, Stavros G. Demos & Robert C. Brasch "In-vivo NIR autofluorescence imaging of rat mammary tumors" Opt. Express, Vol. 14, No. 15, pages 6713-6723, 2006.

Figure 1:
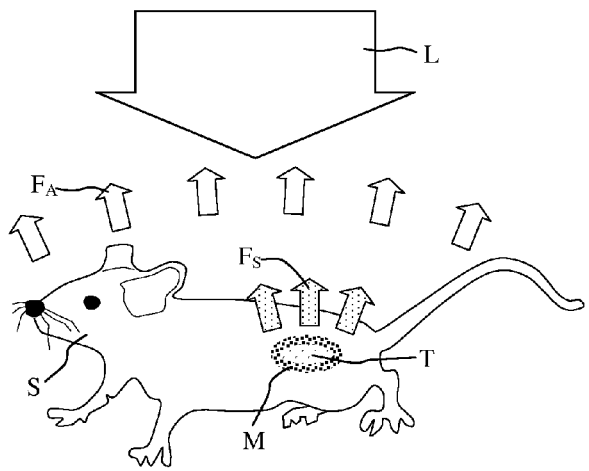
FIG. 1 is a schematic illustration of the phenomenon of autofluorescence.
Figure 2A:
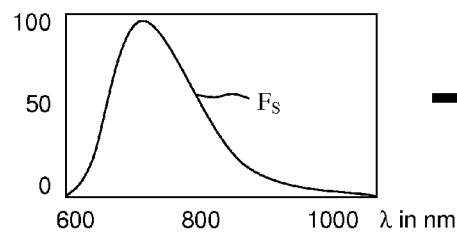
FIGS. 2A, 2B and 2C show schematically the spectral distribution of the fluorescence of a biological tissue under illumination by a wavelength located in the red.
Figure 2B:
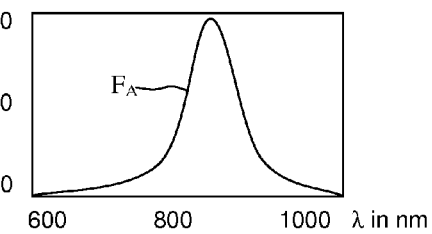
Figure 2C:
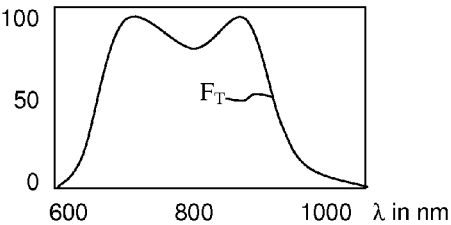
Figure 3:
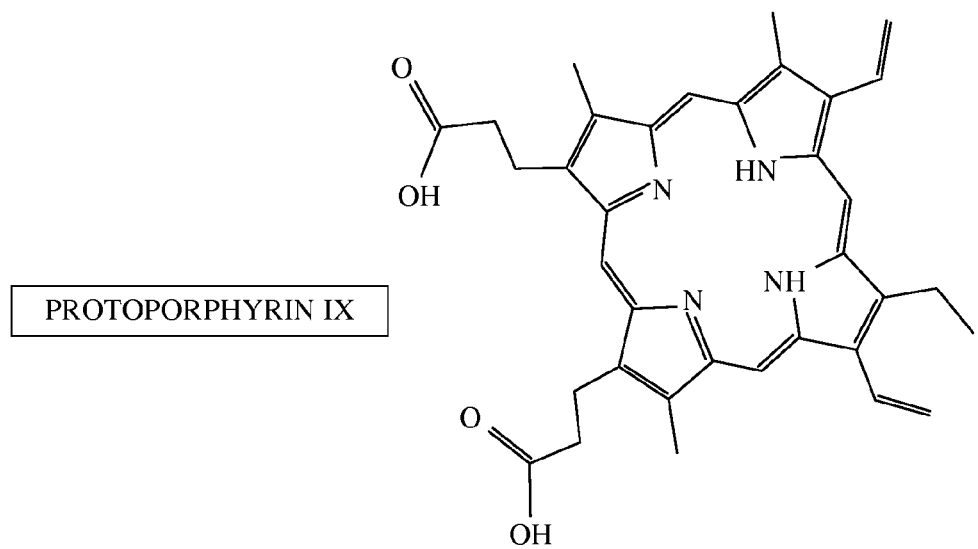
FIG. 3 shows the molecule of protoporphyrin IX.

For information, the molecule of protoporphyrin IX is shown in FIG. 3.

As a non-limiting example, a phantom P according to the invention comprises a matrix composed essentially of water, of Intralipid which conventionally reproduces the diffusion of tissues, of ink to simulate the absorption of tissues and of food-grade gelatin in order to obtain a semi-solid consistency. As has been mentioned, it is possible to use other diffusers such as paint or particles of oxide and/or other viscosity additives such as agarose gel or PVA (polyvinyl alcohol). Of course, there are also matrices of phantoms that are far more elaborate, using blood to simulate the absorption of haemoglobin. Reference may be made, on this point, to the article with the title "Tissue-Like Phantoms for Near-Infrared Fluorescence Imaging System Assessment and the Training of Surgeons", Alec M. De Grand and John V. Frangioni, 2006. The applicant proposes to add protoporphyrin IX, also called PpIX, to this matrix, to simulate the spectral properties of fluorescence.

To produce a phantom according to the invention, simulating the spectrum and intensity of the autofluorescence signal from a mouse, the approximate quantities required are as follows, for a volume of water of 100 millilitres:

Protoporphyrin PpIX≈3 to 6 mg

Diffuser: Intralipid 20%≈5 to 6 ml

Absorber: Ink in an amount varying depending on the required absorption, about 1 to 2 µl to obtain a phantom whose coefficient of absorption is 0.04 $cm^{-1}$.

Viscosity additive: Sheets of food-grade gelatin, in an amount from 2 to 4 sheets, or about 3.8 to 7.6 g of gelatin (fewer sheets result in a phantom that is more "friable", which does not "hold" for as long). The gelatin used is of porcine origin but other types of gelatin can be used.

The method of production is as follows:
heating the volume of water to a temperature between 30 and 40 degrees;
addition of the sheets of gelatin softened in said volume of water and mixing until the sheets have melted completely, the amount of gelatin being between 4 to 8% of the volume of water;
cooling the water-gelatin mixture to room temperature;
addition of an amount of Intralipid 20% (lipid emulsion based on soya oil) between 4 to 8%, preferably 5 to 6% of the volume of water;
addition of Protoporphyrin PpIX (Supplier: the company Sigma Aldrich);
cooling the water-gelatin-Intralipid-porphyrin mixture to a temperature of about 4° C. until the mixture hardens;
removal of the mixture from the mould.

Addition of Protoporphyrin PpIX makes it possible to obtain, between 600 nm and 900 nm, a fluorescence spectrum close to the spectrum of autofluorescence of the tissues, when excitation uses a red wavelength, typically between 620 and 800 nm. "Spectrum" means a distribution of the relative intensities of the signal detected.

Figure 6:
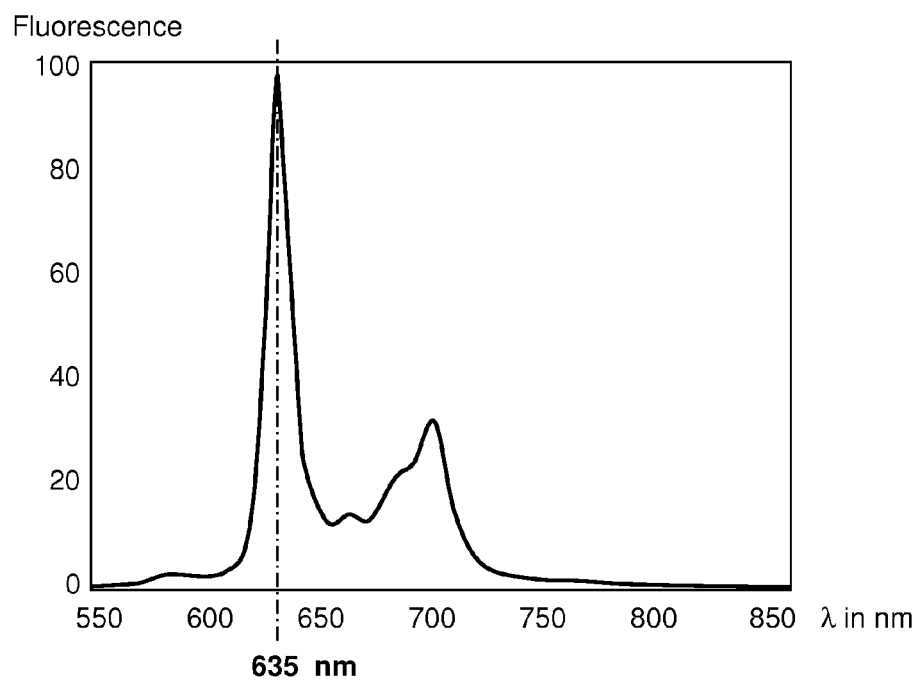
FIG. 6 shows the spectrum of fluorescence of the protoporphyrin.
Figure 7:
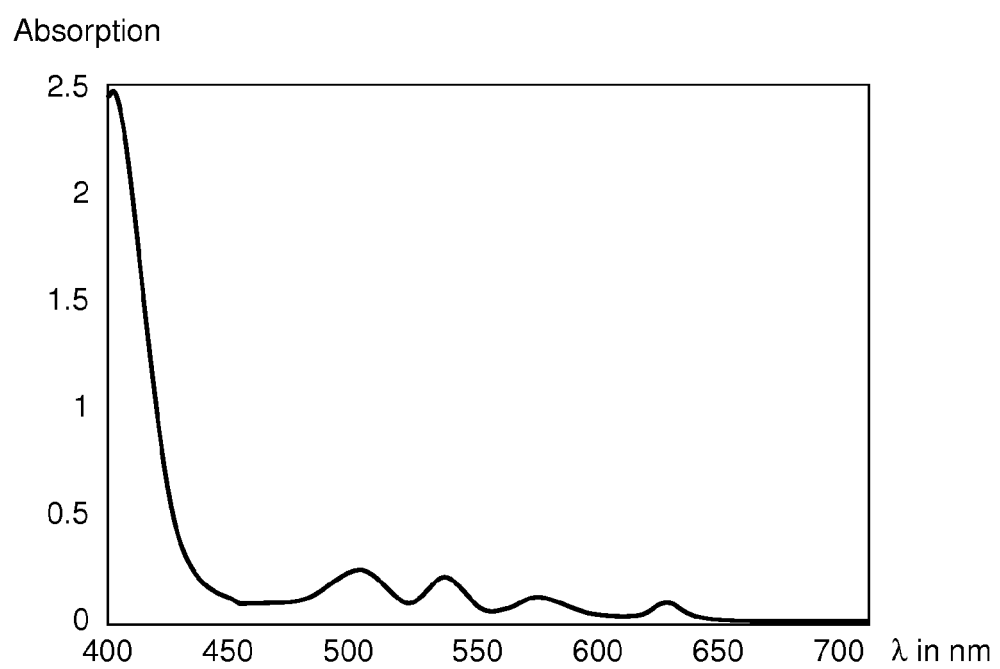
FIG. 7 shows the spectrum of absorption of the protoporphyrin.

The fluorescence properties of Protoporphyrin PpIX are known; the fluorescence spectrum has a fluorescence peak at 630 nm (see FIG. 6), and the fluorescence signal beyond 700 nm is negligible. It is also known that to obtain said fluorescence of Protoporphyrin PpIX, the excitation wavelengths are selected in relation to the absorption spectrum of Protoporphyrin, which has a main peak centred on a wavelength of about 400 nm, and some secondary peaks between 500 and 600 nm (see FIG. 7). Thus, when we wish to observe the fluorescence of Protoporphyrin PpIX, it is customary to use excitation wavelengths in the UV or near UV. Documents DE19855853 and WO2008028298 describe this approach.

The applicant showed that, surprisingly, by exciting a phantom comprising Protoporphyrin PpIX at red or near infrared wavelengths, an emission signal is obtained whose spectrum is near that of the autofluorescence of biological tissues. This effect is manifested notably when protoporphyrin PpIX is added to a viscosity additive, a hydrogel, an agarose gel, gelatin or PVA.

The amount stated in the above example makes it possible to obtain a phantom displaying, under given excitation radiation, a fluorescence signal whose intensity corresponds to the intensity of the autofluorescence signal produced by a mouse submitted to the same excitation radiation.

Of course, when a tissue is to be simulated, for example a breast, a prostate, a brain, a testicle, the concentration of Protoporphyrin PpIX must be adjusted so that, during exposure to a given excitation radiation, the intensity of the fluorescence signal is close to the intensity of the autofluorescence signal of said tissue submitted to the same excitation radiation.

The same applies to the concentrations of the absorber (for example Indian ink) or diffuser (for example Intralipid), the concentrations of which are adjusted in relation to the respective values of the coefficient of absorption and the coefficient of diffusion of the simulated tissue. Depending on the tissues observed, the coefficient of absorption and the reduced coefficient of attenuation, respectively designated $\mu_a$ and $\mu'_s$, vary between 0.01 and 1 $cm^{-1}$ and between 5 and 50 $cm^{-1}$ respectively, in the spectral window of interest.

Moreover, the concentration of viscosity additive is adjusted to the required viscosity of the phantom.

Figure 4:
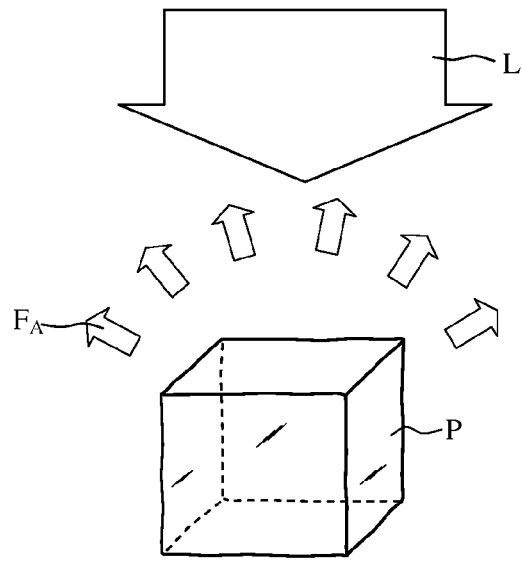
FIG. 4 shows a phantom according to the invention, illuminated in the spectral window of interest.

This phantom is still fairly fragile but can be used for series of manipulations for some days, which is sufficient for many applications. It must be stored in a cool place to avoid degradation of the Intralipid and gelatin. More complex production, by techniques known by a person skilled in the art, can produce phantoms that are more solid and have a longer life. Such a phantom P is shown in FIG. 4. In this diagram, it is of a cubic shape. It can be given other more complex shapes, or even assemblies can be produced comprising several phantoms having different compositions for the best possible simulation of an organ or of a collection of organs and tissues. It is also possible to add tumour simulators to it, for example in the form of inclusions of fluorophores in a capillary.

Figure 5:
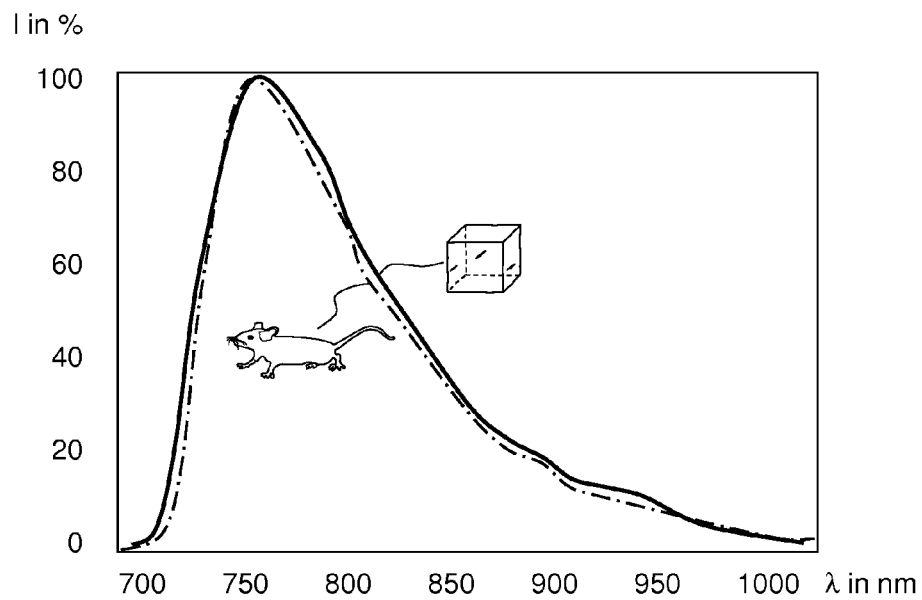
FIG. 5 shows the spectrum of autofluorescence of a living tissue under red illumination and the spectrum of a phantom according to the invention, submitted to the same illumination.

When this phantom is illuminated with red light, for example at 690 nm, represented by a descending arrow in FIG. 4, this phantom emits in the red and near infrared. The intensity I of the spectrum of this radiation $F_A$ shown as a continuous line in FIG. 5, in the range of wavelengths between 700 and 1000 nanometres, is very close to that of the spectrum emitted by an animal (in this case a mouse), the spectrum of which is shown by the dotted lines in FIG. 5. In this diagram, the intensities have been standardized: the spectra therefore correspond to the distribution of the measured relative intensities.

Thus, for the price of a simple procedure, it is possible to produce a phantom having the required autofluorescence properties in the red and near infrared.

Such a phantom can be used during tests or during calibration of optical devices for measuring the fluorescence of tissues.

The invention claimed is:

1. A method of calibrating instrumentation for medical imaging using a calibration device also called a "phantom" comprising a matrix, the matrix comprising at least one additive belonging to the porphyrin class, wherein, during a step of the calibration, the calibration device is illuminated with excitation red light for simulating the auto fluorescence properties of an organ or a living tissue in the spectral band covering the red and near infrared, the excitation red light being between 620 nm and 800 nm.

2. The method of calibrating instrumentation for medical imaging according to claim 1, wherein the additive is protoporphyrin IX.

3. The method of calibrating instrumentation for medical imaging according to claim 1, wherein the proportion of additive in the matrix is between 1 and 1000 millionths.

4. The method of calibrating instrumentation for medical imaging according to claim 1, wherein the proportion of additive in the matrix is between 1 and 100 millionths.

5. The method of calibrating instrumentation for medical imaging according to claim 1, wherein the proportion of additive in the matrix is between 30 and 60 millionths.

6. The method of calibrating instrumentation for medical imaging according to claim 1, wherein the matrix is an aqueous solution.

7. The method of calibrating instrumentation for medical imaging according to claim 1, wherein the matrix comprises an absorber for simulating optical absorption.

8. The method of calibrating instrumentation for medical imaging according to claim 7, wherein the absorber is Indian ink or haemoglobin.

9. The method of calibrating instrumentation for medical imaging according to claim 1, wherein the matrix comprises a diffuser for simulating optical diffusion.

10. The method of calibrating instrumentation for medical imaging according to claim 9, wherein the diffuser is white paint or particles of oxide.

11. The method of calibrating instrumentation for medical imaging according to claim 1, wherein the matrix comprises a viscosity additive which increases the viscosity of the calibration device.

12. The method of calibrating instrumentation for medical imaging according to claim 11, wherein the viscosity additive is a hydrogel or agarose gel or PVA (polyvinyl alcohol) or gelatin.

13. The method of calibrating instrumentation for medical imaging according to claim 1, wherein the calibration device contains a tumour simulator.

* * * * *